Figure 1:
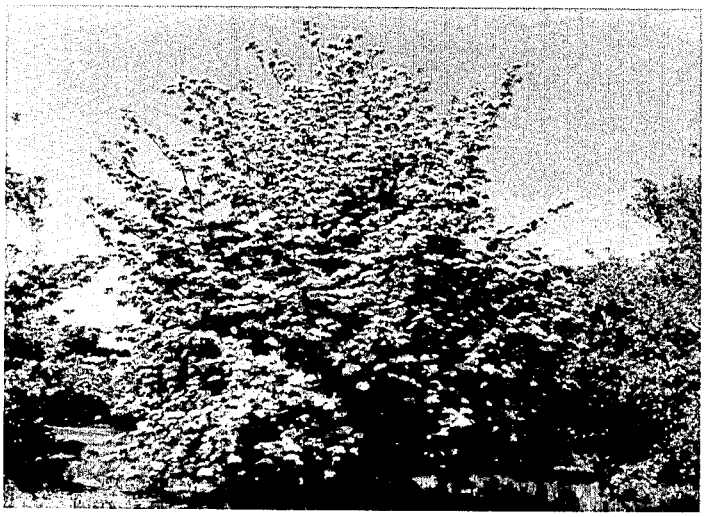

United States Patent [19]

Orton, Jr.

[11] Patent Number: Plant 7,205

[45] Date of Patent: Mar. 27, 1990

[54] DOGWOOD TREE "AURORA"

[75] Inventor: Elwin R. Orton, Jr., Somerville, N.J.

[73] Assignee: Rutgers University, New Brunswick, N.J.

[21] Appl. No.: 262,595

[22] Filed: Oct. 26, 1988

[51] Int. Cl.[4] ..... A01H 5/00

[52] U.S. Cl. ..... Plt./51

[58] Field of Search ..... Plt./51

*Primary Examiner*—James R. Feyrer

*Attorney, Agent, or Firm*—Frank B. Robb

[57] ABSTRACT

A hybrid of *Cornus kousa* Hance and *Cornus florida* L. providing a new large-bracted dogwood, which is an exceptionally vigorous, highly floriferous, small, flowering tree, more nearly like *C. kousa,* being upright in habit rather than low and spreading like *C. florida,* yet more fully branched and spreading as compared with *C. kousa* and having a period of floral display that is intermediate to *C. florida* and *C. kousa,* exhibiting highly textured, rounded and overlapping white floral bracts that are larger than those of either parent plant.

2 Drawing Sheets

BACKGROUND OF THE DISCLOSURE

This invention relates to a large-bracted dogwood cultivar, which is one of those developed in an extensive program or interspecific hybridization, in an effort to produce characteristics which I believe are desirable in dogwood trees and the results have justified my efforts I believe.

The particular cultivar hereof, as one of a series of dogwood trees resulting from an extensive period of development, embodies my ideas of desirability and other characteristics which make the same commercially attractive and thereby having substantial potential for commercial distribution.

Some of the characteristics which I have provided as a result of my program, and which this particular cultivar exhibits, include an upright habit and a much larger tree than certain low spreading plants of which a companion plant Cornus X 'Rutfan' (unpatented) is exemplary. Other plants developed generally during the same period of time are somewhat similar in upright habit but differ in possessing floral bracts of different size, shape, texture and/or color.

This particular cultivar as before suggested, is one of a group which will be referred to in general and in some instances specifically, by comparison for identification and other purposes.

Since the instant cultivar which I have chosen to designate for commercial identification as 'Rutban', is one of a number of dogwood cultivars which I have developed, it will be compared in many instances herein with certain of the others which are also designated by their commercial names though none is as yet patented.

It will be understood that the parental species *C. florida* and *C. kousa* have been used as a basis for the cultivars referred to and thus many of the characteristics will be found as common, yet each in turn is distinctive in its own way.

I note that plants of this species combination have not been reported previously, to my knowledge.

Field plantings of the instant cultivar 'Rutban' in the vicinity of New Brunswick, N.J., do not reveal infestation by the dogwood borer nor have they exhibited "dogwood decline".

I am thus of the opinion that the plant 'Rutban', hereof may be grown wherever plants of the parental species *C. florida* and/or *C. kousa* are able to be grown and will exhibit the desirable characteristics and distinctions set forth herein.

Plants of my new cultivar 'Aurora' are upright in habit and much larger than the low spreading plants of another of my so far unpatented cultivar developments, Cornus×'Rutfan', are similar to plants I have developed, Cornus×'Rutcan' in upright habit but differing in possessing large, rounded, overlapping floral bracts rather than narrow floral bracts. They are also similar to another of my plants Cornus×'Rutdan' in upright habit, time of flowering, and shape of the floral bracts, but exhibit more vigor and produce larger and more heavily textured floral bracts. My new cultivar is similar in habit to yet another of my developments, Cornus×'Rutgan' in plant habit but produces larger, rounded, heavily textured, white floral bracts as opposed to the smaller, pink floral bracts of 'Stellar Pink'.

My new hybrid is highly sterile.

In order to summarize the various characteristics which are notable in my new cultivar, I have broken down the aspects of the same regarding tree shape, flower buds, bracts and other characteristics which will be set forth hereinafter in the specific succinct summaries noted below.

I have caused the cultivar of my new dogwood tree to be reproduced asexually by grafting, budding or rooting of stem cuttings and found that it retains its distinguishing characteristics from generation to generation.

FIG. 1 discloses a tree of my new cultivar in full.

Figure 2:
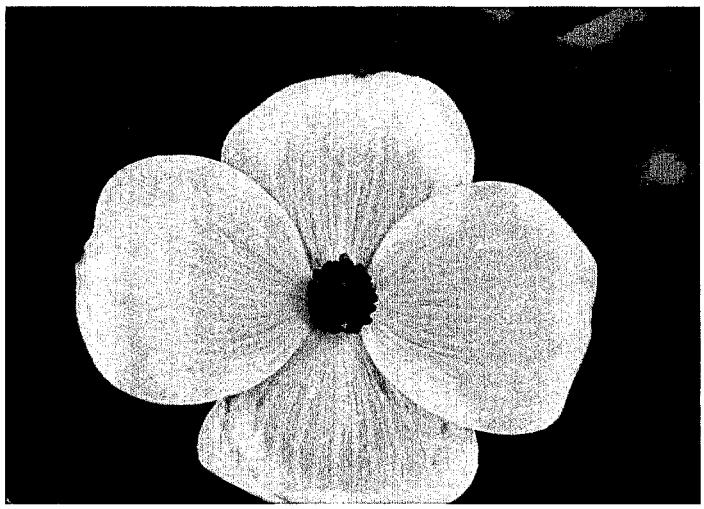

FIG. 2 discloses four floral bracts with central subtended flower heads, typical of my new cultivar.

Where color is referred to, The Royal Horticultural Society Colour Chart is availed of and the colors are as nearly true as is possible to make the same in an illustration of this character, made by photographic means.

Tree: The tree disclosed in the drawing is about 17 years old, 5.86 meters tall, with a spread of 5.71 meters. Exceptionally vigorous — upright — vase shaped when young, but soon becomes dense and full — Hardy Very productive; i.e., very floriferous (but highly sterile) regular bearer.

Trunk: Medium — smooth when young but becoming shaggy with age, as then exhibits exfoliating bark.

Branches: Medium — smooth.

Lenticels: Numerous — medium.

Leaves: Abundant.

*Length.*—9.7–15.5 cm (average=12.4).

*Width.*—4.3–7.6 cm (average=6.1). Medium size — elliptic with acuminate tip and an asymmetric cuneate base — medium. Dark green: Upper surface R.H.S. 139A (Green Group). Lower surface R.H.S. 138B (Green Group). Slightly undulate margin.

Petiole: Short: 7–15 mm (average=10.7 mm).

Flowers buds: (The True flowers are small and numerous and are borne in flower heads. They are relatively inconspicuous. The floral display is provided by large floral bracts that subtend the flower heads. In common terminology and usually in the art, the floral bracts are described as though they were the flowers.) Hardy; in U.S.D.A. Plant Hardiness Zone 6a (−10 degrees F.). Medium size (larger than those of *C. kousa* but smaller than those of *C. florida;* plump; covered with light brown pubescence.

Floral bracts:

| | Color: | | |
|---|---|---|---|
| | Start of floral display | Midseason floral display | Peak of floral display |
| Upper Surface | 154C Yellow-Green Group | 150D Yellow-Green Group | 157A Green-White Group |
| Lower Surface | 154D Yellow-Green | 150D Yellow-Green | 157B Green-White |

*Size.*—Larger than those of typical plants of either parent species, *C. kousa* or *C. florida.* When the floral bracts are fully expanded, the diameter of the inflorescence from tip to tip of the opposing inner bracts is about 131 mm; the diameter of the inflorescence as measured from tip to tip of the opposing outer bracts is about 115 mm. The average length of the inner bracts is approximately 65 mm; the average length of the outer bracts is approximately 56 mm. The average width of the inner bracts at their widest point is 51 mm. The average width of the outer bracts at their widest point is 59 mm. Bract length and width can vary considerably from year to year, but the inner bracts most likely will be longer and narrower than the outer bracts in any given year. Bracts are sessile, heavily textured, nearly rounded to obovate with broad, tapering bases and acute tips; the outer or lower bracts are shorter and wider than the inner bracts and are nearly truncate at the apex. The margins of the basal one-third of adjacent bracts typically overlap.

*Peduncle length.*—Each flower head is borne on a peduncle, the average length being about 5.8 cm at the time of flowering; whereas those of the *C. kousa* parent average about 7.3 cm in length and those of the *C. florida* parent average about 3.7 at the time of flowering. Absolute peduncle length varies from year to year, but the relative peduncle length of the two parents and that of my new hybrid should be quite consistent from year to year.

Flowers: Anthesis of the tiny, relatively inconspicuous true flowers generally commences two to four days after the onset of the ornamental display of the large floral bracts. The average number of true flowers per flower head (45.5) in my new hybrid is intermediate to that for the *C. kousa* parent (average=49) and that for the *C. florida* parent (average 25.7). Flowering period is early compared to plants of *C. kousa* and late compared with plants of *C. florida.* Period of floral display (floral bracts) is intermediate to that of plants of the parent species; i.e., occurs in mid-May, commencing one to three days after completion of the floral display (floral bracts) of most plants of *C. florida* and ending a few days after the start of the floral display (floral bracts) of many plants of *C. kousa.*

Fruit: Fully developed fruit have not been observed, as plants of this new $F_1$ interspecific hybrid are highly sterile. However, the flower heads often persist throughout the growing season and, occasionally, the fleshy portion of small parthenocarpic (seedless) fruit will develop, albeit incompletely. However, there is no formation of a syncarp as in *C. kousa,* as the flowers in this new hybrid are distinct and separate in the flower head, or on the receptacle.

Resistance to:

*Insects.*—Good. In field plantings with *C. kousa* and *C. florida,* the Dogwood Borer has ravaged the plants of *C. florida,* but has not infested plants of my new $F_1$ interspecific hybrid.

*Disease.*—Good. In field plantings with *C. florida* and *C. kousa,* my new $F_1$ interspecific hybrid has been free of the "dogwood decline" that has decimated cultivated and wild stands of *C. florida* in recent years.

I claim:

1. A new and distinct cultivar of dogwood tree, substantially as herein shown and described, characterized particularly as to novelty by the unique combination of its exceptionally high vigor and highly floriferous small flowering form, similar to its seed parent as to its upright, vase-shaped habit when young, becoming more fully branched and spreading with age, intermediate the two parents as to characteristics of the overwintering flower buds and time of flowering, exhibiting floral bracts of a size exceeding that of either parent as well as that of most plants of either parental species, and exhibits resistance to dogwood borers and "dogwood decline".

* * * * *

UNITED STATES PATENT AND TRADEMARK OFFICE

CERTIFICATE OF CORRECTION

PATENT NO. : Plant 7,205

DATED : March 27, 1990

INVENTOR(S) : Elwin R. Orton, Jr.

It is certified that error appears in the above-identified patent and that said Letters Patent is hereby corrected as shown below:

On tile page, 'AURORA' should read –'RUTBAN'–;
and at Column 2, line 3, 'AURORA' should read –'RUTBAN'–.

Signed and Sealed this

Twenty-seventh Day of July, 1999

*Attest:*

Q. TODD DICKINSON

*Attesting Officer*

*Acting Commissioner of Patents and Trademarks*